US00PP33629P2

(12) United States Plant Patent
Hartman

(10) Patent No.: US PP33,629 P2
(45) Date of Patent: Nov. 9, 2021

(54) ***CALADIUM* PLANT NAMED 'LWH OF13-332'**

(50) Latin Name: ***Caladium* X *hortulanum***
Varietal Denomination: LWH OF13-332

(71) Applicant: Robert Dale Hartman, Lake Placid, FL (US)

(72) Inventor: Robert Dale Hartman, Lake Placid, FL (US)

( * ) Notice: Subject to any disclaimer, the term of this patent is extended or adjusted under 35 U.S.C. 154(b) by 0 days.

(21) Appl. No.: 17/013,793

(22) Filed: Sep. 7, 2020

(51) Int. Cl.
*A01H 5/12* (2018.01)
*A01H 6/10* (2018.01)
*A01H 6/00* (2018.01)

(52) U.S. Cl.
USPC ..... Plt./373
CPC ..... *A01H 6/00* (2018.05)

(58) Field of Classification Search
USPC ..... Plt./263.1, 373
See application file for complete search history.

*Primary Examiner* — Susan McCormick Ewoldt
*Assistant Examiner* — Karen M Redden
(74) *Attorney, Agent, or Firm* — C. Anne Whealy

(57) ABSTRACT

A new and distinct cultivar of *Caladium* plant named 'LWH OF13-332', characterized by its intermediate height; mounding plant habit; dense and bushy appearance; vigorous growth habit and rapid growth rate; lance-type leaves that are light red to variable shades of pink in color with random green and orange-colored spots with dark bronze red-colored venation and margins; and petioles that are black or black with tannish pink stripes in color.

6 Drawing Sheets

Figure 1:
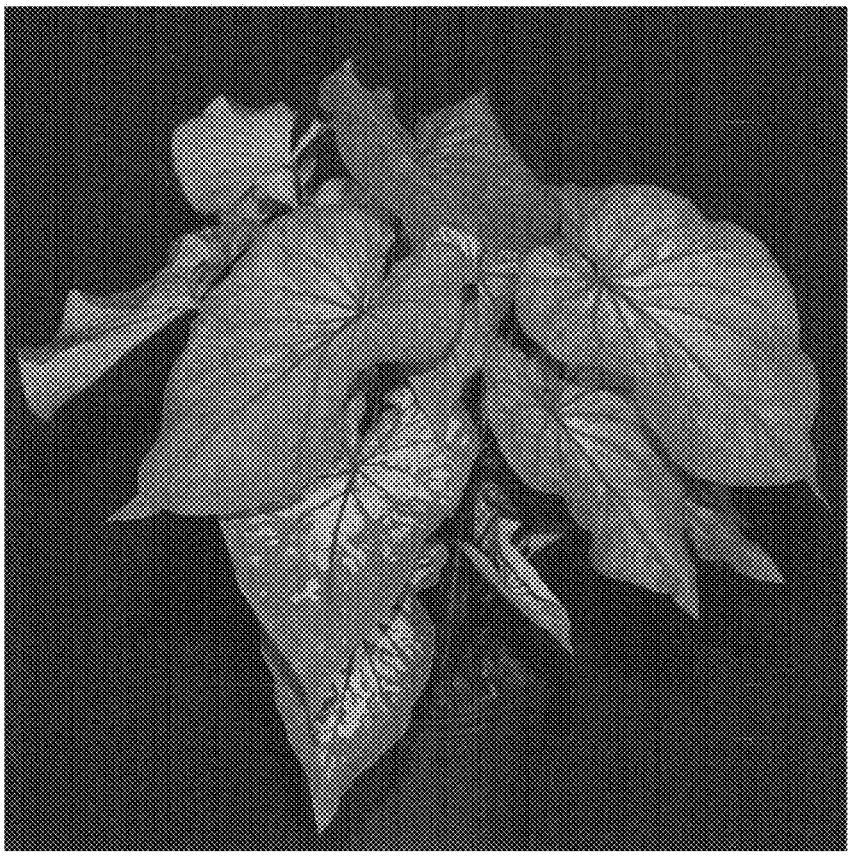

Botanical designation: *Caladium* X *hortulanum*.
Cultivar denomination: 'LWH OF13-332'.

STATEMENT REGARDING PRIOR DISCLOSURES BY INVENTOR/APPLICANT

The Inventor/Applicant asserts that no publications nor advertisements relating to sales, offers for sale or public distribution occurred more than one year prior to the effective filing date of this application. Any information about the claimed plant would have been obtained from a direct or indirect disclosure from the Inventor. Applicant claims a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Caladium* plant, botanically known as *Caladium* X *hortulanum*, commercially referred to as a lance leaf-type *Caladium* and hereinafter referred to by the name 'LWH OF13-332'.

The objective of the Inventor's breeding program is to create new *Caladium* plants that have uniform plant habit, exceptional container and garden performance and attractive and unique leaf coloration.

The new *Caladium* plant originated from a cross-pollination made by the Inventor in April, 2012 in Avon Park, Fla. of *Caladium* X *hortulanum* 'Florida Sweetheart', disclosed in U.S. Plant Pat. No. 8,526, as the female, or seed, parent with *Caladium* X *hortulanum* 'Scarlet Flame', disclosed in U.S. Plant Pat. No. 25,419, as the male, or pollen, parent. The new *Caladium* plant was discovered and selected by the Inventor as a single plant within the progeny of the stated cross-pollination in a controlled outdoor nursery environment in Avon Park, Fla. in September, 2013.

Asexual reproduction of the new *Caladium* plant by "chipping" the tubers (cutting the tuber into segments with each segment containing an axillary bud and tuber cortical tissue) in a controlled outdoor nursery environment in Zolfo Springs, Fla. since April, 2014 has shown that the unique features of this new *Caladium* plant are stable and reproduced true to type in successive generations of asexual reproduction.

SUMMARY OF THE INVENTION

Plants of the new *Caladium* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'LWH OF13-332'. These characteristics in combination distinguish 'LWH OF13-332' as a new and distinct *Caladium* plant:

1. Intermediate in height and mounding plant habit; dense and bushy appearance.
2. Vigorous growth habit and rapid growth rate.
3. Lance-type leaves that are light red to variable shades of pink in color with random green and orange-colored spots with dark bronze red-colored venation and margins.
4. Petioles that are black or black with tannish pink stripes in color.

Plants of the new *Caladium* differ primarily from plants of the female parent, 'Florida Sweetheart', in the following characteristics:

1. Plants of the new *Caladium* and 'Florida Sweetheart' differ in leaf color as leaves of the new *Caladium* are light red to variable shades of pink in color with random green and orange-colored spots with dark bronze red-colored venation and margins whereas leaves of 'Florida Sweetheart' have dark pink-colored venation, rose pink-colored interveinal areas with greenish white-colored margins.

2. Plants of the new *Caladium* and 'Florida Sweetheart' differ in leaf petiole color as leaf petioles of the new *Caladium* are black or black with tannish pink stripes in color whereas leaf petioles of 'Florida Sweetheart' are tannish pink in color with darker-colored stripes.

Plants of the new *Caladium* differ primarily from plants of the male parent, 'Scarlet Flame', in the following characteristics:

1. Plants of the new *Caladium* are taller than plants of 'Scarlet Flame'.
2. Plants of the new *Caladium* and 'Scarlet Flame' differ in leaf color as leaves of the new *Caladium* are light red to variable shades of pink in color with random green and orange-colored spots with dark bronze red-colored venation and margins whereas leaves of 'Scarlet Flame' are dark green in color with rose red-colored venation and pink and rose red-colored spots and blotches.
3. Plants of the new *Caladium* and 'Scarlet Flame' differ in leaf petiole color as leaf petioles of the new *Caladium* are black or black with tannish pink stripes in color whereas leaf petioles of 'Scarlet Flame' are tannish green in color with black-colored streaks.

Plants of the new *Caladium* can be compared to plants of *Caladium* X *hortulanum* 'Caribbean Coral', disclosed in U.S. Plant Pat. No. 29,546. In side-by-side comparisons, plants of the new *Caladium* differ primarily from plants of 'Caribbean Coral' in the following characteristics:

1. Plants of the new *Caladium* and 'Caribbean Coral' differ in leaf color as leaves of the new *Caladium* are light red to variable shades of pink in color with random green and orange-colored spots with dark bronze red-colored venation and margins whereas leaves of 'Caribbean Coral' are dark olive green in color with dark pink-colored venation surrounded with lighter pink areas and interveinal areas that are pink variably suffused with green in color with random greenish white and pink-colored spots.
2. Plants of the new *Caladium* and 'Caribbean Coral' differ in leaf petiole color as leaf petioles of the new *Caladium* are black or black with tannish pink stripes in color whereas leaf petioles of 'Caribbean Coral' are tannish pink in color tinged with a brownish green-colored cast.

Plants of the new *Caladium* can also be compared to plants of *Caladium* X *hortulanum* 'Blushing Bride', disclosed in U.S. Plant Pat. No. 22,213. In side-by-side comparisons, plants of the new *Caladium* differ primarily from plants of 'Blushing Bride' in the following characteristics:

1. Plants of the new *Caladium* and 'Blushing Bride' differ in leaf color as leaves of the new *Caladium* are light red to variable shades of pink in color with random green and orange-colored spots with dark bronze red-colored venation and margins whereas leaves of 'Blushing Bride' are greyed purple in color with dark green-colored margins and whitish-colored venation tinged with greyed purple.
2. Plants of the new *Caladium* and 'Blushing Bride' differ in leaf petiole color as leaf petioles of the new *Caladium* are black or black with tannish pink stripes in color whereas leaf petioles of 'Blushing Bride' are tannish pink to tannish green in color with dark brownish green-colored stippling, streaks and tessellations.

BRIEF DESCRIPTION OF THE PHOTOGRAPHS

The accompanying photographs illustrate the overall appearance of the new *Caladium* plant showing the colors as true as it is reasonably possible to obtain in colored reproductions of this type. Colors in the photographs may differ slightly from the color values cited in the detailed botanical description which accurately describe the colors of the new *Caladium* plant.

The photograph on the first sheet (FIG. 1) is a side perspective view of a typical plant of 'LWH OF13-332' in a container and grown in a shade house (tuber de-eyed).

Figure 2:
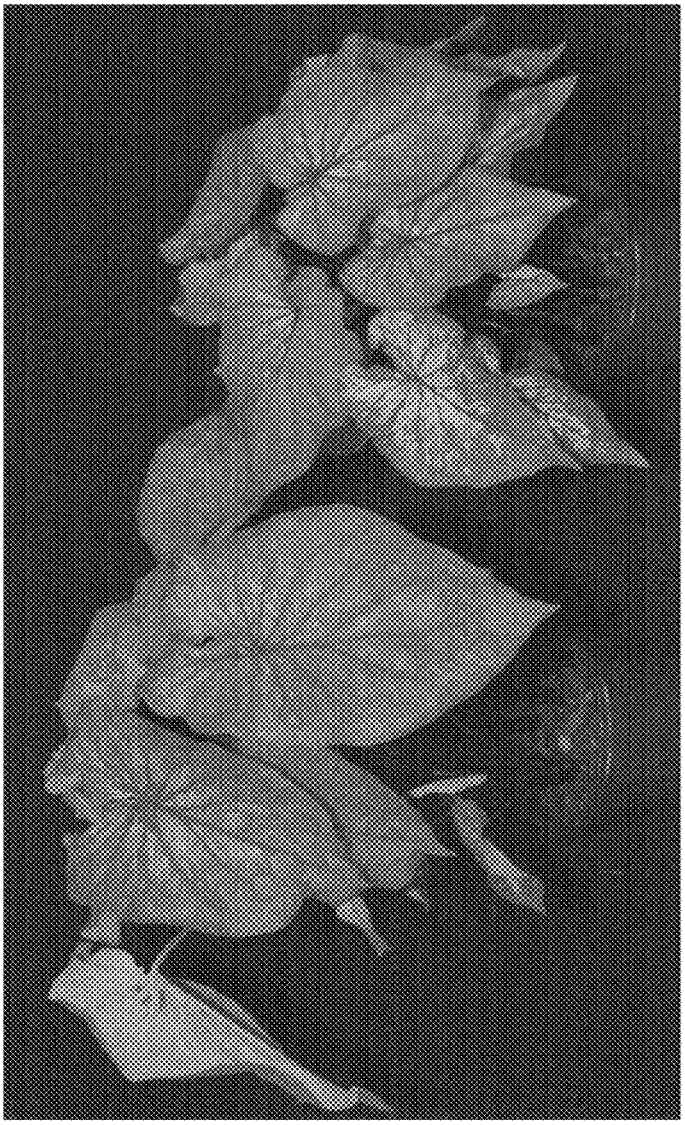
Figure 3:
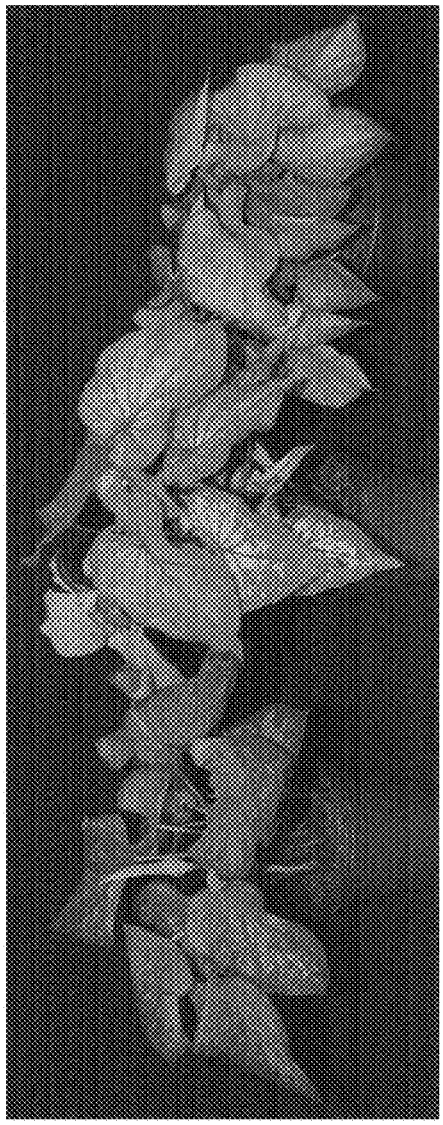

The photograph on the second sheet (FIG. 2) is a comparison view of typical plants of 'LWH OF13-332' grown in containers, the plant on the left has not had its tuber de-eyed and the plant on the right has had its tuber de-eyed prior to planting; the photograph on the third sheet (FIG. 3) is side perspective view of the male parent, 'Scarlet Flame' (left), 'LWH OF13-332' (center) and the female parent, 'Florida Sweetheart' (right).

Figure 4:
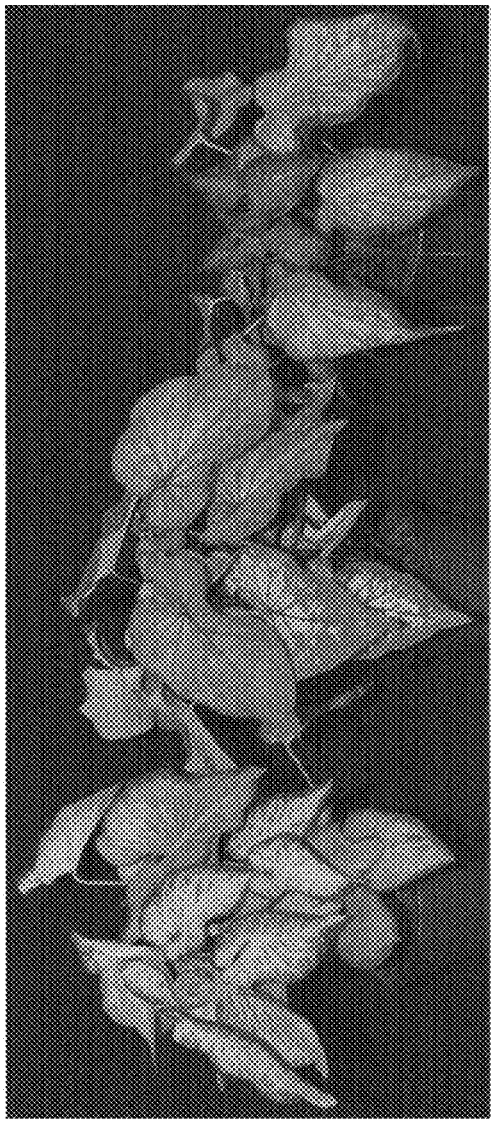

The photograph on the fourth sheet (FIG. 4) is a comparison view of typical potted plants of 'Blushing Bride' (left), 'LWH OF13-332' (center) and 'Caribbean Coral' (right).

Figure 5:
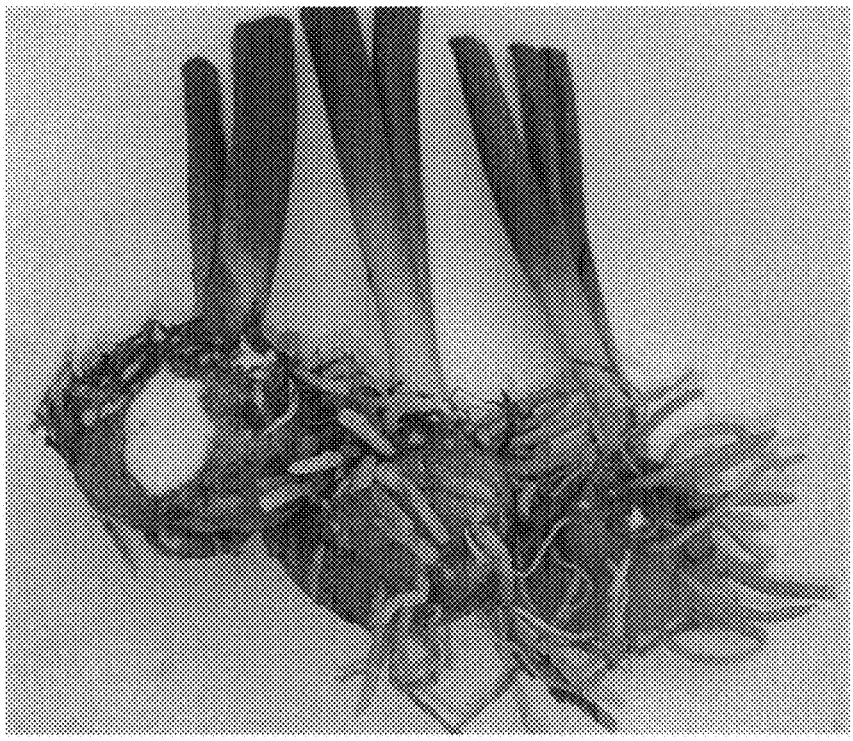

The photograph on the fifth sheet (FIG. 5) is a close-up view of typical freshly-harvested tubers with roots and leaf petioles of 'LWH OF13-332'.

Figure 6:
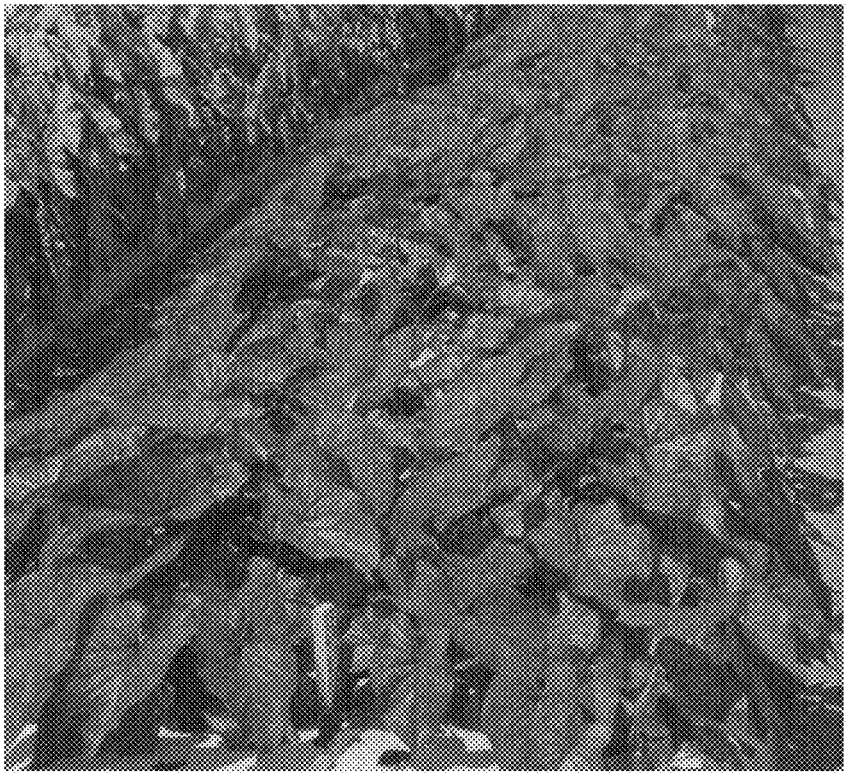

The photograph on the sixth sheet (FIG. 6) is a side perspective view of typical plants of 'LWH OF13-332' grown in an open production field.

DETAILED BOTANICAL DESCRIPTION

The aforementioned photographs and following observations and measurements describe plants grown in 15-cm containers in a polypropylene-covered shade house (30% light reduction) in Avon Park, Fla. and plants grown in ground beds under full sunlight conditions in an outdoor nursery in Crewsville, Fla. The plants were grown under cultural practices typical of commercial shade house and outdoor nursery production. During the production of the shade house-grown plants, day temperatures ranged from about 28° C. to 33° C., night temperatures ranged from about 22° C. to 25° C. and light levels were about 8,000 foot-candles. During the production of the outdoor nursery-grown plants, day temperatures ranged from about 29° C. to 35° C., night temperatures ranged from about 23° C. to 26° C. and light levels ranged from 10,000 to 12,000 foot-candles. Plants grown in the shade house were five weeks old and plants grown in the outdoor nursery were six months old when the photographs and the detailed description were taken. In the following description, color references are made to The Royal Horticultural Society Colour Chart, 2015 Edition, except where general terms of ordinary dictionary significance are used.

Botanical classification: *Caladium* X *hortulanum* 'LWH OF13-332'.

Parentage:

*Female, or seed, parent.*—*Caladium* X *hortulanum* 'Florida Sweetheart', disclosed in U.S. Plant Pat. No. 8,526.

*Male, or pollen, parent.*—*Caladium* X *hortulanum* 'Scarlet Flame', disclosed in U.S. Plant Pat. No. 25,419.

Propagation:

*Type*.—By "chipping" the tubers.

*Time to initiate roots, summer*.—About seven to ten days at temperatures about 32° C.

*Time to initiate roots, winter*.—About two to three weeks at temperatures about 24° C.

*Tuber description* (*outdoor nursery-grown plants*).—Appearance: Multi-segmented; individual segments elliptic in shape. Height: About 3.1 cm. Diameter: About 7.7 cm to 10.1 cm. Segment height: About 2.3 cm. Segment diameter: About 3.9 cm. Axillary bud shape: Roughly triangular. Axillary bud size: About 3.5 mm by 4 mm. Texture: Thick, starchy; somewhat brittle. Color: Periderm, freshly-harvested: Close to 199A and 199B. Periderm, dried: Close to 200A to 200B. Epidermis: Initially, close to 158B becoming closer to 155A with development. Cortical tissue: Close to 1C and 1D. Axillary buds: Close to 56C and 56D occasionally tinged with close to N186A. Root description: Thick, fleshy contractile roots with few lateral branches; color, close to N155D. Rooting habit: Medium density.

Plant description:

*Plant type*.—Herbaceous perennial; suitable as a potted plant in containers 15-cm to 25-cm and suitable as a landscape plant in shaded areas.

*Plant and growth habit*.—Intermediate in height, upright and mounding plant habit; dense and bushy appearance; vigorous growth habit and rapid growth rate; potted plants finish in saleable form in about four to five weeks after planting tubers; leaf petioles and leaves arise from one or more growing points on tubers; leaf petioles initially upright and leaning outwardly with development.

*Plant height, from soil level to top of foliar plane, shade house-grown potted plants, tubers de-eyed*.—About 37 cm to 39 cm.

*Plant height, from soil level to top of foliar plane, shade house-grown potted plants, tubers not de-eyed*.—About 47.5 cm to 51 cm.

*Plant diameter or spread, shade house-grown potted plants, tubers de-eyed*.—About 36 cm to 43 cm.

*Plant diameter or spread, shade house-grown potted plants, tubers not de-eyed*.—About 56 cm.

*Number of shoots per plant, shade house-grown potted plants, tubers de-eyed*.—About 10 to 13 develop per #1 tuber.

*Number of shoots per plant, shade house-grown potted plants, tubers not de-eyed*.—About two to three develop per #1 tuber.

*Cataphylls, shade house-grown potted plants*.—Length: About 6 cm to 8 cm. Width: About 1.4 cm. Shape: Elliptic to linear. Apex: Acute, emarginate, variable. Base: Sheathing the stem. Color: Outer surface: Close to 177D densely streaked and stippled with close to N199A and N200A; color becoming closer to 200A to 200B with development. Inner surface: Close to N155B; colors and patterns on outer surface visible on inner surface.

Leaf description:

*Arrangement and type*.—Alternate; simple; lance-type.

*Length, shade house-grown potted plants, tubers de-eyed*.—About 16.5 cm to 17 cm.

*Length, shade house-grown potted plants, tubers not de-eyed*.—About 18.2 cm to 26 cm.

*Width, shade house-grown potted plants, tubers de-eyed*.—About 10.5 cm to 14.5 cm; when flattened, about 11.5 cm to 16 cm.

*Width, shade house-grown potted plants, tubers not de-eyed*.—About 12 cm to 16 cm; when flattened, about 13 cm to 18 cm.

*Shape*.—Broadly ovate.

*Apex*.—Acuminate, cuspidate.

*Base*.—Sagittate-peltate, cordate.

*Margin*.—Entire; somewhat wavy with broad undulations.

*Texture and luster, upper surface*.—Smooth, glabrous; leathery; dull sheen.

*Texture and luster, lower surface*.—Smooth, glabrous; glaucous; dull sheen.

*Venation pattern*.—Pinnate and palmate.

*Color, shade house-grown potted plants*.—Fully developed leaves, upper surface: Background (interveinal areas) color: Close to 50A, 50B, 51B, 62C, 62D, 147A, and 147A flushed with close to 178A; random spots, close to 147A, 48B and 49A. Margins: Close to 183A and N186C with random flecks, close to 184A and 184B; leaf edge, close to 48A. Basal notch: Close to 187C. Midvein and primary venation: Close to 183B and N186C. Secondary venation: Close to 147A and 183A. Fully developed leaves, lower surface: Background (interveinal areas) color: Close to 63B, 63C, 63D, 147B, 196C and close to N155A tinged with close to 62D; random spots, close to 62D, 63D, 186B and 186D. Margins: Close to 191A tinged with close to 194A; random spots, close to 62D, 63D, 186B and 186D; leaf edge, close to 183A. Basal notch: Close to 187B. Leaf attachment point: Close to N186C. Midvein: Close to 199B with streaks and markings, close to N199A and N199B. Primary and secondary venation: Close to 191C, N148C to N148D, 199A and 183A; areas surrounding venation, close to 196A, 196C and 147B with flecks, close to 183C.

*Petioles*.—Aspect: Initially upright and straight and leaning outwardly with development; flexible. Length, shade house-grown potted plants, tubers de-eyed: About 30 cm to 34.5 cm. Length, shade house-grown potted plants, tubers not de-eyed: About 36 cm to 42.5 cm. Diameter, distally, shade house-grown potted plants: About 4 mm to 5 mm. Diameter, proximally, shade house-grown potted plants: About 6 mm to 8 mm. Texture and luster: Smooth, glabrous; slightly glaucous. Color, shade house-grown potted plants: When developing and fully developed: Close to 203A tinged with close to N200A or close to 203B tinged with N200A, striped, streaked and mottled with close to 164D and N170D; just below the leaf junction, close to 203A tinged with close to N200A and streaked with close to 179D. Wing length, shade house-grown potted plants: About 6.8 cm to 10.8 cm. Wing diameter, shade house-grown potted plants: About 8 mm to 11 mm. Texture and luster, inner surface: Smooth, glabrous; glossy. Texture and luster, outer surface: Smooth, glabrous; dull sheen. Wing color, shade house-grown potted plants: Outer surface: Close to 147A flushed with close to N200A, marbled and streaked with close to N155B. Inner surface: Close to N155B; colors and patterns on the outer surface are visible on the inner surface.

Inflorescence description: To date, inflorescence development has not been observed on plants of the new *Caladium*.

Pathogen & pest tolerance: Plants of the new *Caladium* have been observed to have average tolerance to *Pythium* Root Rot and above average tolerance to *Xanthomonas* Leaf Spot. Plants of the new *Caladium* have not been observed to have resistance to pests and other pathogens common to *Caladium* plants.

Temperature tolerance: Plants of the new *Caladium* have been observed to tolerate temperatures ranging from about 7° C. to about 40° C. and are suitable for USDA Hardiness Zones 8A to 11. In cooler zones, tubers can be "lifted" prior to first freeze and stored in a cool dry environment to overwinter for re-planting the following spring.

It is claimed:

1. A new and distinct *Caladium* plant named 'LWH OF13-332' as illustrated and described.

* * * * *